United States Patent [19]

Waldmann-Laue et al.

[11] Patent Number: 5,539,001
[45] Date of Patent: Jul. 23, 1996

[54] ANTIMICROBIAL MIXTURES

[75] Inventors: Marianne Waldmann-Laue, Monheim; Irina Slominski, Essen; Gerhard Stoll, Korschenbroich; Bernhard Meyer, Mettman; Werner Schneider, Krefeld, all of Germany

[73] Assignee: Henkel Kommanditgesellschaft auf Aktien, Duesseldorf, Germany

[21] Appl. No.: 182,170

[22] PCT Filed: Jul. 16, 1992

[86] PCT No.: PCT/EP92/01618

§ 371 Date: Feb. 15, 1994

§ 102(e) Date: Feb. 15, 1994

[87] PCT Pub. No.: WO93/01714

PCT Pub. Date: Feb. 4, 1993

[30] Foreign Application Priority Data

Jul. 25, 1991 [DE] Germany .................. 41 24 664.0

[51] Int. Cl.$^6$ .................. A01N 31/00; A01N 31/14; A61K 31/08; A61K 31/045
[52] U.S. Cl. .................. 514/723; 514/730; 514/738
[58] Field of Search .................. 514/730, 723, 514/738

[56] References Cited

U.S. PATENT DOCUMENTS

| | | | |
|---|---|---|---|
| 2,255,916 | 9/1941 | Doelling | 167/22 |
| 3,502,594 | 3/1970 | Ahrens | 252/404 |
| 3,652,764 | 3/1972 | Lamberti et al. | 424/235 |
| 4,321,257 | 3/1982 | Sipos | 424/80 |
| 5,104,447 | 4/1992 | Stewart et al. | 106/2 |

FOREIGN PATENT DOCUMENTS

| | | |
|---|---|---|
| 0166611 | 1/1986 | European Pat. Off. . |
| 2204943 | 8/1973 | Germany . |
| 4026756 | 2/1992 | Germany . |
| 51-091327 | 8/1976 | Japan . |

OTHER PUBLICATIONS

M. A. L. Mackie et al., Pharm. Acta Helv. 61, Nr. 12 (1986).
Journal of Food Science, vol. 42, (1977) No. 3, S. 699–706.
Jp 76/91327, Chem. Abstr. 85, 117980r (1976) (Nishizawa et al).
R. R. Egan, "Cosmetics and Perfumery" 88, Mar. 1973, pp. 45–50.

*Primary Examiner*—Allen J. Robinson
*Attorney, Agent, or Firm*—Wayne C. Jaeschke; J. Daniel Wood; Daniel S. Ortiz

[57] ABSTRACT

Antimicrobial mixtures containing specific antimicrobial diols, e.g. 1,2-dodecanediol, and specific aromatic alcohols, e.g. phenylethyl alcohol or hydrocinnamic alcohol, are provided. Such mixtures with a weight ratio of diol to aromatic alcohol of 9:1 to 1:9 have been found to exhibit a synergistic effect, i.e. a high antimicrobial activity which cannot be explained by an additive effect of the very low-activity components. Such mixtures are useful in the disinfection of hard surfaces, in the production of disinfectant cleaning preparations and in the preservation of water-based preparations of microbially degradable substances.

11 Claims, No Drawings

ANTIMICROBIAL MIXTURES

This application is a 371 of PCT/EP92/01618 filed Jul. 16, 1992.

FIELD OF THE INVENTION

1. Background of the Invention

This invention relates to antimicrobial mixtures containing antimicrobial diols and aromatic alcohols.

2. Discussion of Related Art

The antimicrobial properties of certain aromatic alcohols, for example benzyl alcohol, have been known for some time (cf. M. A. L. Mackie et al., Pharm. Acta Helv. 61, No. 12, (1986). Long-chain linear 1,2- and 1,3-diols have certain germ-inhibiting properties (cf. Journal of Food Science, Vol. 42 (1977), No. 3, 699–706, DE-OS 22 04 943 and JP 76/91327, Chem. Abstr. 85, 117980r (1976)).

However, the antimicrobial properties of these substances are by no means pronounced, so that the safe preservation of microbially perishable preparations is only possible with unacceptably high concentrations of these substances.

In the field of disinfectants and preservatives, there is a considerable need—for reasons of pollution control, physiological compatibility and economy—for antimicrobial substances and combinations thereof which show adequate antimicrobial activity, even in low in-use concentrations. This applies in particular to the preservation of personal hygiene and body-care preparations. Synergistic combinations of known and physiologically safe active substances are of particular value in this regard.

SUMMARY OF THE INVENTION

It has been found that mixtures containing (A) at least one antimicrobial alcohol corresponding to formula I:

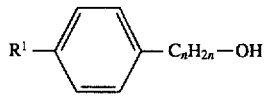
(I)

in which $R^1$ is hydrogen or a $C_{1-4}$ alkyl group and n is an integer of 1 to 6, and (B) at least one antimicrobial 1,2- or 1,3-diol corresponding to formula II:

$$R^2\text{—CHOH—}(CHR^3)_x\text{—}CH_2OH \quad (II)$$

in which $x=0$ or 1 and, where $x=0$, $R^2$ is a $C_{6-22}$ alkyl group or an alkoxymethyl or 2-hydroxyalkoxymethyl group containing 6 to 22 carbon atoms in the alkoxy group and, where $x=1$, $R^2$ is hydrogen and $R^3$ has one of the meanings mentioned above for $R^2$, components (A) and (B) being present in a ratio by weight of (A) to (B) of 9:1 to 1:9, show surprisingly high antimicrobial activity which cannot be explained by an additive effect of the very low-activity individual components.

Mixtures such as these are the subject of the present invention and may be formulated, for example, as concentrates in a suitable carrier and used for the disinfection of hard surfaces, for the production of disinfectant cleaning preparations or for the preservation of water-based preparations of microbially degradable substances.

DETAILED DESCRIPTION OF THE INVENTION

The mixtures according to the invention are preferably used for the preservation of water-based preparations of microbially degradable substances.

Suitable carriers for the formulation of the mixtures according to the invention are, for example, lower alcohols, such as ethanol and isopropanol, or polyols, such as 1,2-propylene glycol, glycerol or liquid polyethylene glycols and mixtures thereof with one another or with water.

Suitable antimicrobial alcohols corresponding to formula I are, for example, benzyl alcohol, phenyl ethanol, phenyl propanol, phenyl butanol, phenyl pentanol and phenyl hexanol. For cosmetic products, some of the products mentioned above have the advantage of an agreeable odor so that further perfuming is either unnecessary or can be obtained with relatively small quantities of other fragrances. This applies above all to alcohols corresponding to formula I in which n=2 or 3, i.e. phenyl ethanol and phenyl propanol (hydrocinnamic alcohol), which are therefore preferred for use in cosmetics.

Suitable antimicrobial diols corresponding to formula II are, in particular, alkane-1,2-diols containing 8 to 24 carbon atoms ($x=0$, $R^2=C_{6-22}$ alkyl), alkane-1,3-diols containing 9 to 25 carbon ($x=1$, $R^2=C_{6-22}$ alkyl, $R^3=H$), glycerol monoalkyl ethers ($x=1$, $R^2=C_{6-22}$ alkoxymethyl, $R^3=H$) and glycerol mono-(2-hydroxy)-alkyl ethers ($x=1$, $R^2=2$-hydroxy-$C_{6-22}$-alkoxymethyl, $R^3=H$) Other suitable diols are the 2-substituted propane-1,3-diols ($x=1$, $R^2=H$, $R^3=C_{6-22}$ alkyl, $C_{6-22}$ 2-hydroxyalkyl, $C_{6-22}$ alkoxymethyl or $C_{6-22}$ 2-hydroxyalkoxymethyl). Diols which are suitable as skin-friendly cosmetic oil components and which therefore perform an additional extremely desirable function when used in cosmetics are particularly preferred. The diols in question are preferably 1,2-diols corresponding to formula II in which $x=0$ and $R^2$ is a $C_{8-14}$ alkyl or alkoxymethyl group. 1,2-Diols such as these and their production are described, for example, by H. Rutzen in Fette, Seifen, Anstrichmittel 82 (1980), No. 1, pages 23 et seq. and are described as very skin-friendly oil components by R. R. Egan in Cosmetics and Perfumery 88, March 1973, 45–50.

A concentrate suitable as a preservative may be prepared, for example, from 10 to 30% by weight of an aromatic alcohol corresponding to formula I 10 to 30% by weight of a diol corresponding to formula II 40 to 80% by weight of one or more polyols from the group consisting of 1,2-propylene glycol, glycerol and polyethylene glycol with an average molecular weight of 200 to 1000.

A concentrate consisting of

20% by weight of phenylethyl alcohol or hydrocinnamic alcohol

20% by weight of 1,2-dodecanediol and

60% by weight of 1,2-propylene glycol is particularly suitable.

The antimicrobial mixtures according to the invention are particularly suitable for the preparation of antiseptic skin cleansing preparations. However, they are particularly suitable for the preservation of aqueous preparations of microbially degradable or perishable substances. These preparations may be, for example, skin cleansing preparations and personal hygiene preparations, but are preferably cosmetic cleansing and body-care emulsions containing microbially degradable oils, fats, proteins, carbohydrates or derivatives thereof. For preservation against bacterial or fungal degradation, these products contain an antimicrobial mixture according to the invention in a quantity corresponding to a content of 0.2 to 5% by weight, based on the sum of components (A+B).

A concentrate containing, for example, 20% by weight of the aromatic alcohol I, 20% by weight of the diol II and 60% by weight of a lower polyol, for example 1,2-propylene glycol, is added to the preparation to be preserved in a quantity of approximately 0.5 to 12% by weight in order to obtain adequate preservation.

The invention is illustrated by the following Examples.

EXAMPLES

Testing of the preserving effect

I Test emulsion

Test emulsions were prepared in accordance with the following formulation:

| | |
|---|---|
| Paraffin oil | 17.0% by weight |
| Isopropyl palmitate | 2.0% by weight |
| Microcrystalline wax | 2.7% by weight |
| Arlacel ® 186 (1) | 2.5 by weight |
| Zincum | 3.0% by weight |
| Magnesium sulfate | 0.5% by weight |
| Glycerol | 3.0% by weight |
| 1,2-Propylene glycol | 2.0% by weight |
| Preservative (combination) | 2.0% by weight |
| Water | 65.3% by weight |

The following products were introduced into the emulsions as preservatives:

A1: phenylethyl alcohol
A2: hydrocinnamic alcohol (3-phenyl-1-propanol)
B1: 1,2-dodecanediol
B2: 1-(2-hydroxydodecyloxy)-2,3-propanediol The composition of the preservative in test emulsions 1 to 8 is shown in Table I.

II Contamination test

The preserving effect was tested in a qualitative contamination test using a mixture of bacteria and fungi. Contamination was carried out with $\geq 10^6$ bacteria/g product and $\geq 10^5$ fungi/g product. The suspension used for contamination was added in a concentration of 1%.

| Test germs: | | |
|---|---|---|
| Bacteria: | *Staphylococcus aureus* | ATCC 6538 |
| | *Enterococcus faecium* | ATCC 6057 |
| | *Escherichia coli* | ATCC 11229 |
| | *Enterobacter aerogenes* | DSM 30053 |
| | *Pseudomonas aeruginosa* | ATCC 15442 |
| Fungi: | *Candida albicans* | ATCC 10231 |
| | *Aspergillus niger* | ATCC 6275 |
| | *Penicillium rubrum* | CMI 113729 |
| | *Trichoderma viride* | BAM T21 |

The contaminated samples were homogenized and stored at room temperature. Samples were taken after 1, 3, 7, 14 and 21 days, inoculated and incubated (fungi on wort agar and broth at 30° C., bacteria on standard I nutrient agar and broth at 37° C.). The period of storage after which germs capable of surviving or proliferating could no longer be detected in a 0.1 g sample is shown in Table I.

TABLE I

| | Example | | | | | | | | | |
|---|---|---|---|---|---|---|---|---|---|---|
| Preservation | 1 | 2 | 3 | 4 | 5 | 6 | 7 | 8 | 9 | 10 |
| A1 % by weight | 2 | — | — | — | 1 | 1 | — | — | 1 | 1 |
| A2 % by weight | — | 2 | — | — | — | — | 1 | 1 | — | — |
| B1 % by weight | — | — | 2 | — | 1 | — | 1 | — | 1 | 1 |
| B2 % by weight | — | — | — | 2 | — | 1 | — | 1 | — | — |
| Destruction time (days) | | | | | | | | | | |
| Fungi | >21 | 22 | 21 | 21 | 14 | 7 | 7 | 14 | 7 | 7 |
| Bacteria | >21 | >21 | >21 | >21 | 3 | 3 | 3 | 1 | 1 | 21 |

Examples 1 to 4 (Comparison Examples) show that the good effect of the combination (A+B) of Examples 5 to 8 is not achieved with components A and B on their own, even when used in the same quantities.

The following emulsions were additionally included in the preservation test:

| Example 9: o/w emulsion | |
|---|---|
| Lameform ® TGi (2) | 1.0% by weight |
| Brij 30 | 1.0% by weight |
| Microcrystalline wax | 0.5% by weight |
| 1,3-Diisooctyl cyclohexane | 10.0% by weight |
| Cetiol SN (3) | 3.0% by weight |
| Avocado oil | 3.0% by weight |
| Magnesium-aluminium silicate (Veegum ®) | 3.6% by weight |
| Xanthan gum | 1.8% by weight |
| Citric acid | 0.13% by weight |
| 1,2-dodecanediol | 1.0% by weight |
| Phenylethyl alcohol | 1.0% by weight |
| Water | ad 100.0% by weight |

In the contamination test, this product had destruction times of 1 day for bacteria and 7 days for fungi.

| Example 10: Shower bath | |
|---|---|
| Fatty alcohol $C_{12/14}$ polyglycol ether (2 EO) sulfate, Na salt, 28% in water | 50.0% by weight |
| Dehyton K (30% in $H_2O$) (4) | 8.0% by weight |
| Nutrilan H (5) | 2.0% by weight |
| Cetiol HE (6) | 2.0% by weight |
| Oleyl alcohol polyglycol (5 EO) ether | 2.0% by weight |
| Merquat ® 550 (quaternium 41) | 1.0% by weight |
| 1,2-Dodecanediol | 1.0% by weight |
| Phenylethyl alcohol | 1.0% by weight |
| Citric acid | 0.11% by weight |
| Water | ad 100.0% by weight |

In the contamination test, this product had destruction times of 21 days for bacteria and 7 days for fungi.

| Example 11: Preservative concentrate | |
|---|---|
| Phenylethyl alcohol | 20% by weight |
| 1,2-Dodecanediol | 20% by weight |
| 1,2-Propylene glycol | 60% by weight |

-continued

| Example 12: Preservative concentrate | |
|---|---|
| Hydrocinnamic alcohol | 20% by weight |
| 1,2-Dodecanediol | 20% by weight |
| 1,2-Propylene glycol | 60% by weight |

The following commercial products were used:

| (1) | Arlacel 186: | Mixture of oleic acid mono-/diglyceride (90%) and 1,2-propylene glycol (10%) |
|---|---|---|
| (2) | Lameform TGi: | Polyglyceryl (3) diisostearate |
| (3) | Cetiol SN: | Cetostearyl isononanoate |
| (4) | Dehyton K: | $RCO-N-(CH_2)_3-N(CH_3)_2-CH_2COO^{(-)}$ (RCO = coconut oil acyl), 30% in water |
| (5) | Nutrilan H: | Protein hydrolysate, Na salt (32% solids in water) |
| (6) | Cetiol HE: | Glycerol polyglycol ether (7 EO) coconut oil fatty acid ester |

We claim:

1. An antimicrobial composition comprising:
a synergistic antimicrobial effective amount of at least one antimicrobial alcohol selected from the group consisting of phenyl ethanol and phenyl propanol and at least one antimicrobial diol selected from the group consisting of 1,2 dodecanediol and 1-(2-hydroxydodecyloxy)-2,3-propanediol, said antimicrobial alcohols and said antimicrobial diols being present in a ratio by weight of 3:1 to 1:3.

2. The composition as claimed in claim 1 wherein said antimicrobial alcohol is at least one of phenyl ethanol or phenyl propanol and said antimicrobial diol is 1,2-dodecanediol.

3. The composition as claimed in claim 1 wherein said antimicrobial alcohol is 10 to 30% by weight of said composition and said antimicrobial diol is 10 to 30% by weight of said composition.

4. The composition as claimed in claim 3 further comprising a carrier selected from the group consisting of lower alcohols, polyols, and mixtures thereof, with one another or with water.

5. The composition as claimed in claim 4 wherein said carrier is at least one member selected from the group consisting of 1,2-propylene glycol, glycerol and polyethylene glycol with an average molecular weight of 200 to 1000.

6. The composition as claimed in claim 5 wherein said carrier comprises from 40 to 80% by weight of said composition.

7. The composition as claimed in claim 5 consisting of 20% by weight of phenylethanol or phenyl propanol 20% by weight of 1,2-dodecanediol, and 60% by weight of 1,2-propylene glycol.

8. A composition for cleansing and care of the body comprising: at least one member selected from the group consisting of microbially degradable diols, fats, proteins, carbohydrates, or a derivative of such member and an amount effective to preserve said member of an antimicrobial composition comprising a synergistic antimicrobial effective amount of at least one antimicrobial alcohol selected from the group consisting of phenyl ethanol and phenyl propanol, and at least one antimicrobial diol selected from the group consisting of 1,2 dodecanediol and 1-(2-hydroxydodecyloxy)-2,3-propanedial, said antimicrobial alcohols and said antimicrobial diols being present in a ratio by weight of 3:1 to 1:3.

9. The composition as claimed in claim 8 wherein said effective amount is 0.2 to 5% by weight based on the sum of the weight of the antimicrobial alcohol and antimicrobial diol.

10. The composition as claimed in claim 8 wherein said antimicrobial diol is 1,2-dodecanediol.

11. The composition as claimed in claim 10 wherein weight ratio of said antimicrobial alcohol to said antimicrobial diol is 1:1.

* * * * *